(12) United States Patent
Palti

(10) Patent No.: US 9,717,473 B2
(45) Date of Patent: Aug. 1, 2017

(54) METHOD AND APPARATUS FOR DETECTING A DIPOLE POSITION MARKER

(71) Applicant: Yoram Palti, Haifa (IL)

(72) Inventor: Yoram Palti, Haifa (IL)

( * ) Notice: Subject to any disclaimer, the term of this patent is extended or adjusted under 35 U.S.C. 154(b) by 629 days.

(21) Appl. No.: 14/179,346

(22) Filed: Feb. 12, 2014

(65) Prior Publication Data

US 2014/0275967 A1    Sep. 18, 2014

Related U.S. Application Data

(60) Provisional application No. 61/764,036, filed on Feb. 13, 2013.

(51) Int. Cl.
| | |
|---|---|
| *A61B 8/00* | (2006.01) |
| *A61B 8/08* | (2006.01) |
| *A61B 90/00* | (2016.01) |
| *A61B 5/00* | (2006.01) |
| *A61B 5/06* | (2006.01) |

(52) U.S. Cl.
CPC .......... *A61B 8/0841* (2013.01); *A61B 8/4461* (2013.01); *A61B 8/488* (2013.01); *A61B 90/39* (2016.02); *A61B 5/064* (2013.01); *A61B 5/6861* (2013.01); *A61B 8/5261* (2013.01); *A61B 2090/3925* (2016.02)

(58) Field of Classification Search
None
See application file for complete search history.

(56) References Cited

U.S. PATENT DOCUMENTS

| | | | |
|---|---|---|---|
| 6,652,452 B1 * | 11/2003 | Seifert | A61B 1/00096 600/140 |
| 2010/0168517 A1 * | 7/2010 | Shim | A61B 1/00016 600/117 |
| 2010/0174189 A1 * | 7/2010 | Abraham | A61B 5/076 600/439 |
| 2011/0144479 A1 * | 6/2011 | Hastings | A61B 1/041 600/424 |

* cited by examiner

*Primary Examiner* — Jonathan Cwern
(74) *Attorney, Agent, or Firm* — Potomac Law Group, PLLC

(57) ABSTRACT

An apparatus, method and system for detecting a position within a body are provided. A dipole that is free to rotate or oscillate within a capsule is inserted at a target location within the body. The dipole can be either electric or magnetic, and the dipole rotates or oscillates within the capsule when an alternating or rotating electric or magnetic field is applied in the vicinity of the dipole. Ultrasound energy is impinged upon the target location and a position of the dipole is determined based on detected ultrasound reflections.

30 Claims, 14 Drawing Sheets

METHOD AND APPARATUS FOR DETECTING A DIPOLE POSITION MARKER

CROSS REFERENCE TO RELATED APPLICATIONS

This Application claims the benefit of U.S. Provisional Application 61/764,036, filed Feb. 13, 2013, which is incorporated herein by reference.

FIELD OF THE INVENTION

The invention relates generally to devices and systems for detecting a position within a body. In particular, the invention relates to inserting an encapsulated dipole within a body, applying an alternating or rotating field in the vicinity of the dipole that causes the dipole to oscillate or rotate, and detecting the position of the dipole based on detected ultrasound reflections from the dipole.

BACKGROUND OF THE INVENTION

Currently, there are numerous situations where a physician may need to know coordinates of a specific area or target within a body. For example, a physician may need to know a particular location in biological tissue and/or an organ relative to a reference point in space. Exemplary situations include the following:

i. Patients may suffer from dangerous arrhythmia caused by a cardiac muscle area that generates abnormal electric signals. The search for, identification and ablation of such malfunctioning cardiac tissue can depend on knowing the location of a selected part of the probe (catheter) used in the ablation procedure. The Carto 3 system manufactured by Webster Biosense and the I Logic system of Super-dimension are examples of systems designed to achieve such localizations;

ii. Lung cancer and other pathologies are often investigated by employing a bronchoscope for visualization, taking a sample (biopsy) for histopathology, excision, etc. In such procedures, the bronchoscope may be guided to the target that is imaged by Cat Scan. Such guidance can depend on continuously knowing the position of the bronchoscope tip position (coordinates) in relation to the target and some reference points. The guidance can be achieved by means such as Electromagnetic navigation (EMN);

iii. During brain surgery, a surgeon may need information regarding a position of a probe or an electrode relative to a surface point and a target area, as in the case of heart described above;

iv. Following several procedures related to prostate hypertrophy or prostate cancer, a physician may need to return to a previously visited site and/or to avoid such a site in a subsequent procedure;

v. Following colostomy or similar procedure in the GI tract, a physician may need to return to the site of resection of a polyp, a malignancy or the site of some other previous manipulation. This need may arise, for example, from the need to perform a resection after receiving the information that the removed tissue includes a malignancy; and/or vi. During procedures involving the ingestion of capsules, such as the Given Imaging PillCam Capsule, it can be important to know the position of the capsule that moves along the GI tract.

Current imaging technologies (e.g., Ultrasound, Cat Scan (CT), and Magnetic Resonance Imaging (MRI)) can enable localization (e.g., position determinations) in cases where the target area has substantially clear recognizable features and/or in cases when a marker (e.g., a metal staple) was left in the target during a previous invasive procedure. However, current imaging technologies can emit harmful radiation (e.g., X-Rays and/or CTs). Current imaging technologies can involve expensive equipment (e.g., MRI), have relatively low resolution and/or can require relatively large markers (e.g., as in the case of ultrasound). Accurate localization using scanning systems such as CT or MRI can rely on generating thin slices of images taken one after the other. Such a procedure is typically not suited as an aid for the various manipulations associated with bronchoscopy and/or cardiac catheterization.

SUMMARY OF THE INVENTION

Advantages of the invention include reduction of pain and harm to a living being due to a reduction in size of a marker. Detecting a velocity of a moving (e.g., rotating) dipole within a capsule allows for the dipole and the capsule to be much smaller than conventional markers. For example, the markers can be sufficiently small to be inserted into the body through a hypodermic needle. Other advantages include detection of a marker without emitting harmful radiation due to the detection being done by ultrasound. The marker can be monitored for long periods of time. Other advantages include a reduction of cost due to, for example, detecting with an ultrasound and/or low cost of manufacturing a small marker having a simple structure. A number of markers can be placed in different positions, each recognizable by the system. The marker can be anchored in a fixed position or free to move with fluid flows within the body.

In one aspect, the invention involves a method of detecting a position within a body. The method involves inserting, at a target location within a body, a dipole that is confined within an internal cavity of a capsule, wherein the dipole is free to oscillate or rotate within the internal cavity. The method also involves applying an electric or a magnetic field in the vicinity of the dipole, wherein the field and the dipole are configured such that the field causes the dipole to oscillate or rotate. The method also involves directing first ultrasound energy at the dipole from a first position outside of the body. The method also involves directing second ultrasound energy at the dipole from a second position outside of the body. The method also involves directing third ultrasound energy at the dipole from a third position outside of the body. The method also involves determining a position of the dipole based on (a) detected reflections of the first ultrasound energy from the dipole, (b) detected reflections of the second ultrasound energy from the dipole, and (c) detected reflections of the third ultrasound energy from the dipole, and (d) knowledge of a relationship between the first position, the second position and the third position.

In some embodiments, the dipole is an electric dipole. In some embodiments, the dipole is a magnetic dipole.

In some embodiments, the determining step uses pulsed ultrasound Doppler to detect time-varying velocities of the dipole, and the position of the dipole is determined based on the detected time-varying velocities In some embodiments, the steps of directing first ultrasound energy, directing second ultrasound energy, and directing third ultrasound energy are performed simultaneously.

In some embodiments, the body is a human being. In some embodiments, the body is an animal. In some embodiments, the body is a member configured to be placed within a living being. In some embodiments, the field is an electric field and the dipole is an electric dipole.

In some embodiments that use an electric field, the field has a magnitude and frequency that does not stimulate biological tissue. In some embodiments, the frequency of the field is greater than 100 kHz. In some embodiments, the first ultrasound energy, the second ultrasound energy and the third ultrasound energy are substantially equal.

In another aspect, the invention features a system for detecting a position within a body. The system includes a capsule that defines a sealed internal cavity, the capsule having a biocompatible outer surface. The system also includes a dipole positioned in the internal cavity, the capsule and the dipole each shaped such that the dipole is capable of oscillating or rotating within the internal cavity in response to an applied field. The system also includes an electric or magnetic field generator that applies, in a target region of the body, a field that causes the dipole to oscillate or rotate within the capsule. The system also includes a first Doppler transmitter and receiver configured to direct first ultrasound energy at the dipole from a first position outside of the body, receive ultrasound reflections from the dipole, and process the reflection using Doppler processing to obtain first velocity data. The system also includes a second Doppler transmitter and receiver configured to direct second ultrasound energy at the dipole from a second position outside of the body, receive ultrasound reflections from the dipole, and process the reflection using Doppler processing to obtain second velocity data. The system also includes a third Doppler transmitter and receiver configured to direct third ultrasound energy at the dipole from a third position outside of the body, receive ultrasound reflections from the dipole, and process the reflection using Doppler processing to obtain third velocity data. The system also includes a triangulation system that determines the position of the dipole based on the first velocity data, the second velocity data, and the third velocity data.

In some embodiments, the dipole is an electric dipole. In some embodiments, the dipole is a magnetic dipole.

In some embodiments, the system includes a probe positioning system that determines the first position, the second position and the third position. In some embodiments, the first position, the second position, and the third position are each input by a user.

In another aspect, the invention includes an apparatus for insertion into biological tissue. The invention includes a capsule that defines a sealed internal cavity, the capsule having a biocompatible outer surface. The invention also includes a dipole positioned in the internal cavity, the capsule and the dipole each shaped such that the dipole is capable of oscillating or rotating within the internal cavity in response to an applied field, the dipole having a length between 0.5 and 1 mm long.

In some embodiments, the invention includes the dipole consists of a biocompatible material. In some embodiments, the internal cavity is substantially spherical. In some embodiments, the internal cavity is substantially elliptical. In some embodiments, the internal cavity is substantially cylindrical.

In some embodiments, the outer surface of the capsule is silicone. In some embodiments, the outer surface of the capsule is carbon. In some embodiments, the outer surface of the capsule is Polytetrafluoroethylene (PTFE), e.g., TEFLON™. In some embodiments, the dipole is a rod. In some embodiments, the dipole is a cross. In some embodiments, the dipole is an elongated ellipse. In some embodiments, the dipole is a rod with spheres attached at each end.

In some embodiments, the dipole is an electric dipole that oscillates or rotates in response to an alternating or rotating electric field. In some embodiments, the dipole is a magnetic dipole that oscillates or rotates in response to an alternating or rotating magnetic field. In some embodiments, the internal cavity is filled with air. In some embodiments, the internal cavity is filled with gas. In some embodiments, the internal cavity holds at least a partial vacuum.

In some embodiments, the dipole comprises a dielectric material that retains an electric charge for at least one month. In some embodiments, the dipole is a synthetic polymer material. In some embodiments, the dipole is Ferroelectric material.

In another aspect, the invention involves a method of detecting a position within a body. The method involves inserting, at a target location within a body, a dipole that is able to oscillate within the body. The method also involves applying an electric or a magnetic field in the vicinity of the dipole, wherein the field and the dipole are configured such that the field causes the dipole to oscillate or rotate. The method also involves directing first ultrasound energy at the dipole from a first position outside of the body. The method also involves directing second ultrasound energy at the dipole from a second position outside of the body. The method also involves directing third ultrasound energy at the dipole from a third position outside of the body. The method also involves determining a position of the dipole based on (a) detected reflections of the first ultrasound energy from the dipole, (b) detected reflections of the second ultrasound energy from the dipole, and (c) detected reflections of the third ultrasound energy from the dipole, and (d) knowledge of a relationship between the first position, the second position and the third position.

In yet another aspect, the invention involves a method of detecting a position within a body. The method involves inserting, at a target location within a body, a dipole that is able to oscillate within the body. The method also involves applying an electric or a magnetic field in the vicinity of the dipole, wherein the field and the dipole are configured such that the field causes the dipole to oscillate or rotate. The method also involves directing first ultrasound energy at the dipole from a first position outside of the body. The method also involves receiving imaging information for the target location. The method also involves determining a position of the dipole based on (a) detected reflections of the first ultrasound energy from the dipole and (b) the imaging information.

In some embodiments, the imaging information is a CAT scan. In some embodiments, the imaging information is a MRI image. In some embodiments, the imaging information is an X-Ray.

In some embodiments, the method also involves directing second ultrasound energy at the dipole from a second position outside of the body and determining a position of the dipole is further based on the detected reflections of the second ultrasound energy from the dipole.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION OF THE INVENTION

In general, the preferred embodiments involve inserting an encapsulated dipole within a body, and impinging a field upon the dipole that causes the dipole to rotate or oscillate (i.e., vibrate) within the capsule. This can be accomplished, for example, by using a magnetic dipole and applying a rotating magnetic field, or using an electric dipole and applying a rotating electric field. Ultrasound transmitter/receiver probes are then used to perform a Doppler detection of the area where the encapsulated dipole was inserted, to detect the velocity of the moving encapsulated dipole within the body. Once the velocity of the encapsulated dipole is detected, the velocity along with probe position information can be used to determine the position of the encapsulated dipole within the body. In alternative embodiments, the dipole is not encapsulated.

Figure 1:
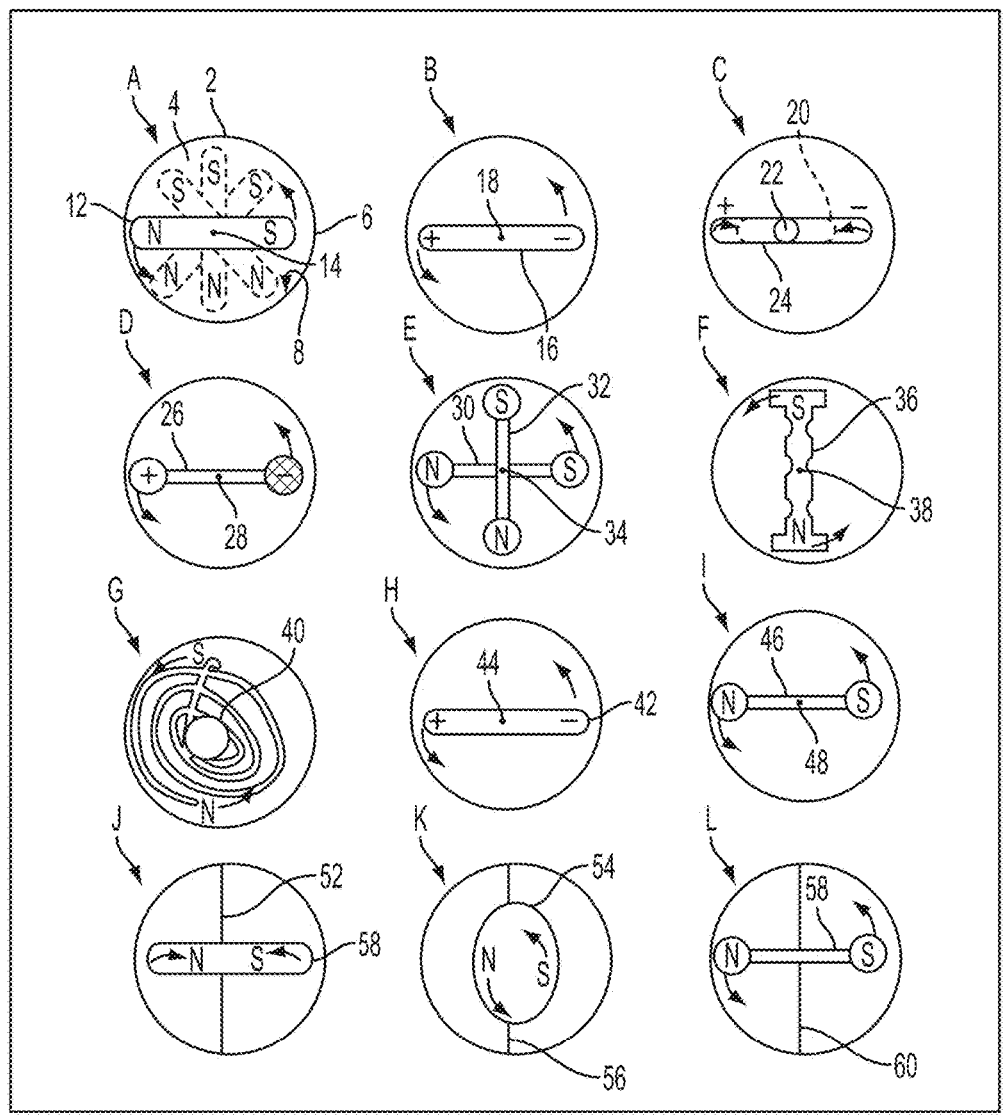
FIG. 1 is a diagram showing various configurations of an encapsulated dipole, according to an illustrative embodiment of the invention.

FIG. 1 is a diagram 100 showing various configurations of encapsulated dipoles, according to illustrative embodiments of the invention. Each configuration of the encapsulated dipoles (A-L) shown in FIG. 1 includes a capsule 2 defining an internal cavity 4, having an outer surface 6, an inner surface 8, and a dipole positioned in the internal cavity 4. For purposes of simplicity, the capsule 2, the outer surface 6, the inner surface 8, and the internal cavity 4 are only shown with numbers for encapsulated dipole A. It is apparent to one of ordinary skill in the art that the capsule numbering for encapsulating dipole A applies equally to encapsulated dipoles (B-L).

In some preferred embodiments, the outer surface 6, the inner surface 8, and/or the whole capsule 2 can be a biocompatible material. In various embodiments, the outer surface 6, the inner surface 8, and/or the whole capsule 2 is silicone, TEFLON™, carbon, or any combination thereof. In various embodiments, the outer surface 6, the inner surface 8, and/or the whole capsule 2 is a material that minimizes reaction of a biological tissue to its presence and at the same time is substantially unaffected by alternating fields.

In various embodiments, the capsule 2 has a spherical shape, an elliptical shape, a cylindrical shape, or any combination thereof. In some embodiments, the capsule 2 has a shape that is suitable for insertion into living body. In some embodiments, the capsule 2 has a shape that is suitable for inserting into a cavity of a living body. For example, the capsule 2 can be shaped for insertion into a gastrointestinal tract, blood vessels and/or heart. In some embodiments, the capsule 2 can be implanted within a tissue or organ during surgery. In various embodiments, the capsule 2 can be inserted into a living body via a small bore hypodermic needle or a catheter.

In some embodiments, the capsule 2 has a diameter less than 1 mm. In various embodiments, the capsule 2 has a length, width, and/or height that is less than 1 mm. In some embodiments, the capsule 2 has a wall thickness under 0.1 mm.

In some embodiments, the capsule 2 is hermetically sealed. In various embodiments, the capsule 2 is evacuated, filled with air, filled with gas, and/or filled with liquid. In various embodiments, the capsule 2 is filled with water, electrolyte, oil, alcohol, silicone, or any combination thereof.

The dipole can be positioned within the cavity 2 such that the dipole is free to rotate or oscillate within the cavity 2. The dipole can be electrically charged or magnetic. Note that throughout the figures, some dipoles are marked as magnetic with N and S, while others are marked as electric with + and −.

In electrically charged dipole embodiments, the dipole can be a dielectric (e.g., insulating) material. In some embodiments, the dipole can be a material that is capable of retaining an electric charge for very long periods of time (e.g., an electret). In some embodiments, the dipole is constructed of materials that have high resistivity (e.g., TEFLON™). In some embodiments, the dipole is any material that can retain an excess charge for at least one month, or even up to many hundreds of years. In various embodiments, the dipole is a synthetic polymer (e.g., fluoropolymers or amorphous polytetrafluoroethylene (PTFE)), polypropylene, polyethyleneterephthalate, or any combination thereof. In various embodiments, the dipole is any Ferroelectrets that displays strong piezoelectricity and is comparable to ceramic piezoelectric materials.

In magnetic dipole embodiments, the dipole can be a ferromagnetic material (e.g., an element associated with being attracted to a magnet and forming an induced magnet, such as iron or steel). In some embodiments, the dipole is a permanent magnet. In various embodiments, the dipole is an alloy of iron, nickel, cobalt, gadolinium, Alnico, neodymium, samarium cobalt, certain ceramic materials, or any combination thereof.

Encapsulated dipole A shows an exemplary magnetic dipole 12 having a rod shape. The magnetic dipole 12 can rotate around an axis 14 within the capsule 2. Encapsulated dipole B shows an exemplary electric dipole 16 having a rod shape. The electric dipole 16 can rotate around an axis 18 within the capsule 2. Encapsulated dipole C shows an exemplary electric dipole 20 that includes a ball 22 within a rod 24. The ball 22 is at the center of the rod 24 and serves as an axis of rotation or oscillation. Encapsulate dipole D shows an exemplary electric dipole 26 that includes a rod with two spherical balls, one on each end of the rod. The electric dipole 26 can rotate around an axis 28.

Encapsulate dipole E shows two exemplary magnetic dipoles, 30 and 32, each including a rod with two spherical balls, a ball on each of the rod. The two magnetic dipoles, 30 and 32, rotate around an axis 34. Encapsulated dipole F shows an exemplary magnetic dipole 36 that is shaped like a jagged rod. The magnetic dipole 36 can rotate around axis 38. Encapsulated dipole G shows an exemplary magnetic dipole 40 having a ball shape. The magnetic dipole 40 can spin around within the internal cavity of the capsule. Encapsulated dipole H shows an exemplary electric dipole 42 having a rod shape. The exemplary dipole 42 can rotate around axis 44.

Encapsulated dipole I shows an exemplary magnetic dipole 46 having a rod shape with two spherical balls, one on each end of the rod. The magnetic dipole 46 can rotate around axis 48. Encapsulated dipole J shows an exemplary magnetic dipole 50 and a rotation bar 52 that is anchored to the inner surface 8 of the capsule 2. The magnetic dipole 50 can rotate around the rotation bar 52.

Encapsulated dipole K shows an exemplary magnetic dipole 54 and a rotation bar 56 that is anchored to the inner surface 8 of the capsule 2. The magnetic dipole 54 can rotate around the rotation bar 52. Encapsulated dipole L shows an exemplary magnetic dipole 58 and a rotation bar 60. The magnetic dipole 58 can rotate around the rotation bar 60.

In some embodiments, the dipole has an axis symmetric structure. An axis symmetric structure can assist in a smooth consistent rotation. As dipoles have two separate poles, and their strength is typically directly proportional to the distance of separation, the dipoles can be constructed so that their poles are positioned at the furthermost positions. In various preferred embodiments, the length of the dipole is between 0.5-1 mm. In various embodiments, the length of the dipole is between 50-200 microns or a few mm long. In various embodiments, diameter of the dipole or width of the dipole is a fraction of a mm.

Figure 2:
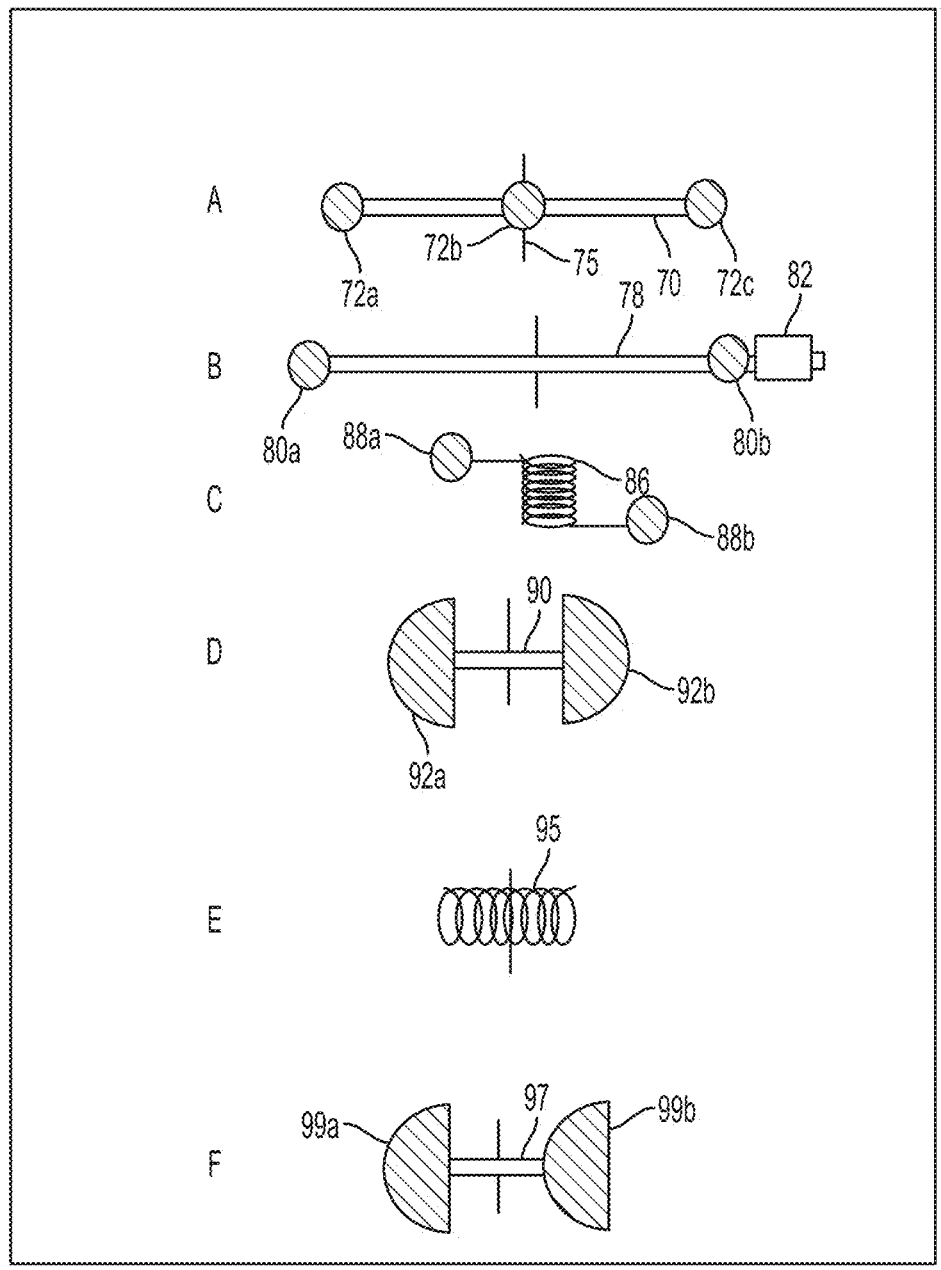
FIG. 2 is a diagram showing various configurations of a dipole, according to illustrative embodiments of the invention.

FIG. 2 is a diagram 200 showing various configurations of a dipole, according to illustrative embodiments of the invention. Dipole A includes a rod 70 and three plastic spheres, 72a, 72b, and 72c, one on each end of the rod 70 and one at the axis of rotation 75. Dipole B includes a rod 78 and two spheres, 80a and 80b, one on each end of the rod 78, and a cork fitting 82. The cork fitting 82 can cause a non-symmetrical signature.

Dipole C includes a coil 86 and two spheres, 88a and 88b, one on each end of the coil 86. Dipole D includes a rod 90 and two half spheres, 92a and 92b, one on each end of the rod 90 with a flat edge of the half sphere facing each other. Dipole E includes a coil 95. Dipole F includes a rod 97 and two half spheres, 99a and 99b, one on each end of the rod 97 with a flat edge of the half sphere facing in the same direction.

Optionally, capsule that encloses the dipole may be filled with fluid. In that case, the dipole will move more slowly, and the field that is applied (discussed below) should preferably vary slower (as compared with the case of empty capsules). The dipole can be free floating within the fluid, and, when appropriate fields are applied, will rotate in the capsule (see, e.g., arrows 34 in FIG. 1B).

During operation, a field is applied to an area where a dipole (or dipoles) is expected to be positioned, such that the field causes the dipole to move. Electric fields are used with electric dipole, and magnetic fields are used with magnetic dipoles. Each of these two scenarios is discussed below. The movement of the dipole will be dependent on a balance between 1) the electric/magnetic forces and 2) friction forces that counter the electric/magnetic forces and which can increase with speed of movement of the dipole.

Figure 3:
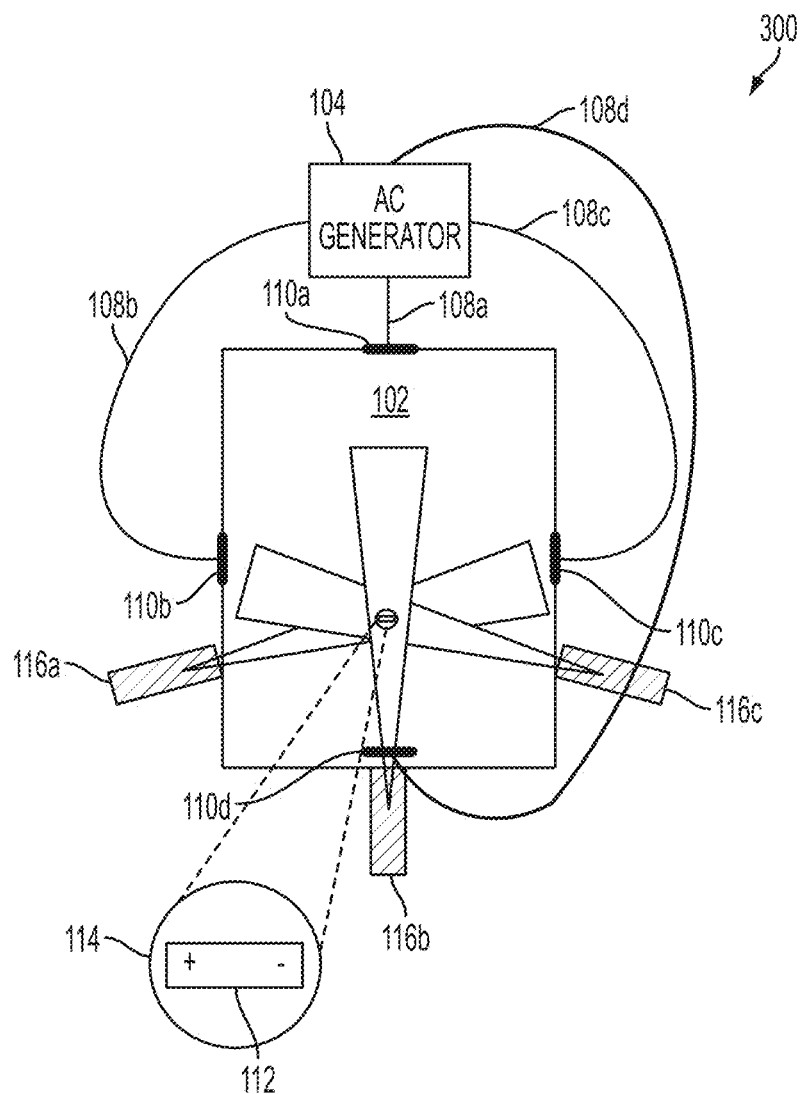
FIG. 3 is a block diagram of an exemplary system for detecting a position within a body, according to an illustrative embodiment of the invention that uses an electric dipole and an electric field.

FIG. 3 is a block diagram of an exemplary system 300 for detecting a position within a body 102, according to an illustrative embodiment of the invention that relies on an electric dipole and electric fields. The system includes an AC electric field generator 104, four leads, 108a, 108b, 108c and 108d, generally, leads 108, that terminate with corresponding contact electrodes 110a, 100b, 100c, and 110d, generally electrodes 110, an electric dipole 112 within a capsule 114, and three Doppler transmitter/receiver probes, 116a, 116b, and 116c, generally Doppler transmitter/receiver probes 116.

The AC electric field generator 104 generates and outputs one or more waveforms through leads 108 to electrodes 110 that are positioned on a surface of the body 102. The voltage and corresponding currents generated by the generator 104 can induce an electric field within the body 102 in an area of the body where the electric dipole 112 within the capsule 114 is located such that the electric dipole 112 moves.

In some embodiments, the location of the electrodes 110 is selected such that the generated electric field periodically changes 180 degrees in direction. For example, the electrodes 110b and 110c can be positioned directly opposite each other, and the electrodes 110a and 110d can be positioned directly opposite each other. In these embodiments, the AC electric field generator 104 supplies a voltage signal to the electrodes 100 that can be a sine wave, a square wave, or any other alternating waveform that causes the electric dipole 112 to move in synchrony with the change in field direction. Electric dipoles can orient themselves along the lines of force of an alternating field. When the alternating field changes orientation in these embodiments, the electric dipole follows and will flip back and forth according to the field polarity. But when the frequency of the alternating field is relatively high (e.g., 100-10,000 Hz) the movement of the dipole may stop (although the alignment of the dipole along the field will remain). Because Doppler-based systems detect velocity, such frequencies should be avoided when an alternating electric field is used.

In other embodiments, the AC electric field generator 104 generates a rotating electric field (e.g., a full 360 degree rotation or partial rotation) within the body of the patient at a selected location. In these embodiments, at least three electrodes are positioned on the body. The rotation can be achieved by applying waveforms (e.g., sinusoids) to the al least three electrodes that are phase shifted with respect to one another to provide a rotating field, in a conventional manner (e.g., similar to the approach used in synchro motors). The rotating electric field within the relevant body volume causes the electric dipole 112 to rotate within the capsule 114.

The rotation of the applied field at an appropriate frequency causes the dipole movement to follow it, at least in part. For example, a rotation rate of 1-10 Hz would be suitable for a dipole that is 1 mm long. The dipole's movement can depend on the applied field strength, a strength of the dipole, a mass of the dipole, and friction forces between the dipole and the capsule. In this respect gas filled capsules can allow a dipole to rotate more easily than in a fluid filled capsule, and a capsule having low friction rotation axis can allow a dipole to rotate more easily than in a capsule having a higher friction rotation axis. Capsules with a complete or partial vacuum inside can also allow a dipole to rotate more easily.

A desired rotation rate for the electric dipole 112 can be based on a movement velocity detection range of the Doppler transmitter/receiver probes 116. In some embodiments, the velocity detection range is 1 cm/sec to 3 m/sec. The velocity detection range can depend on the detection distance. In view of the detection distances required normally within the human body, the preferable the velocity range is about 1-100 cm/sec. A maximum dipole velocity can depend on both a desired rotation rate and the effective dipole length. For example the maximal velocity (e.g., when the movement direction is parallel to the ultrasound beam) of the outer tip of a 1 cm long rod rotating at 60 RPM is about 3 cm/s. All other things held constant, the smaller the dipole length, the faster the rotation speed will be.

In embodiments where the body 102 is a living being, the electrodes 110 can be in contact with the skin by using a gel that does not attenuate the field. In embodiments where the body 102 is a living being, the frequency and amplitude of the induced electric field is preferably selected such that it does not stimulate nerves, muscles and excitable organ (e.g., the heart or nervous system). For example, electric fields of low frequencies, i.e. 1-100 Hz can stimulate nerve and muscle. To avoid such stimulation, low amplitude fields (i.e., sub-threshold) should be used at these frequencies. Typical field thresholds for these low frequencies are: 0.1 V/cm or lower. Higher AC frequencies (e.g., 10 kHz-100 kHz and upward) have much lower stimulating powers such that fields of 1-10 V/cm can be used. Fields having even higher frequency (e.g., >100 kHz) alternating voltage and current are typically safe for a living being at even higher amplitudes.

The preferred Doppler transmitter/receiver probes 116 are single element pulsed Doppler probes (as opposed to phased array probes) that generate ultrasound energy (e.g., ultrasound beams/pulses) and detect the returning echo. In these embodiments, the single element transmits ultrasound beams that are substantially parallel or slightly divergent because, for example, the dipole can be located at different distances from the probes 116 and the reflected energies can be relatively large. In order to accurately locate the target, short ultrasound pulses are preferable (e.g., on the order of 1-5 cycles at 2 MHz) with closely spaced gates (e.g., with spacing of 0.1-0.3 mm) used together with triangulation. Preferably, at least three probes are positioned at appropriate positions (e.g., as shown in FIG. 3) such that the reflections can be used in triangulation. In other embodiments, a single probe may be positioned at at least three locations sequentially. Impedance matching between the probe and skin is preferably achieved using standard ultrasound gel.

In some embodiments, commercially available pulsed ultrasound Doppler systems, e.g., TCD systems that have numerous gates like the Sonara/tec (distributed by Viasys), which has 256 gates can be used. In alternative embodiments, a modified TCD systems may be used, the modified TCD system is substantially similar to a conventional TCD system, but modified so that at least three inputs that can be activated simultaneously using separate probes, in which one can scan all gates independently and view the velocity traces of selected gates. Optionally, in such systems, the corresponding reflected power traces may be displayed.

Figure 4:
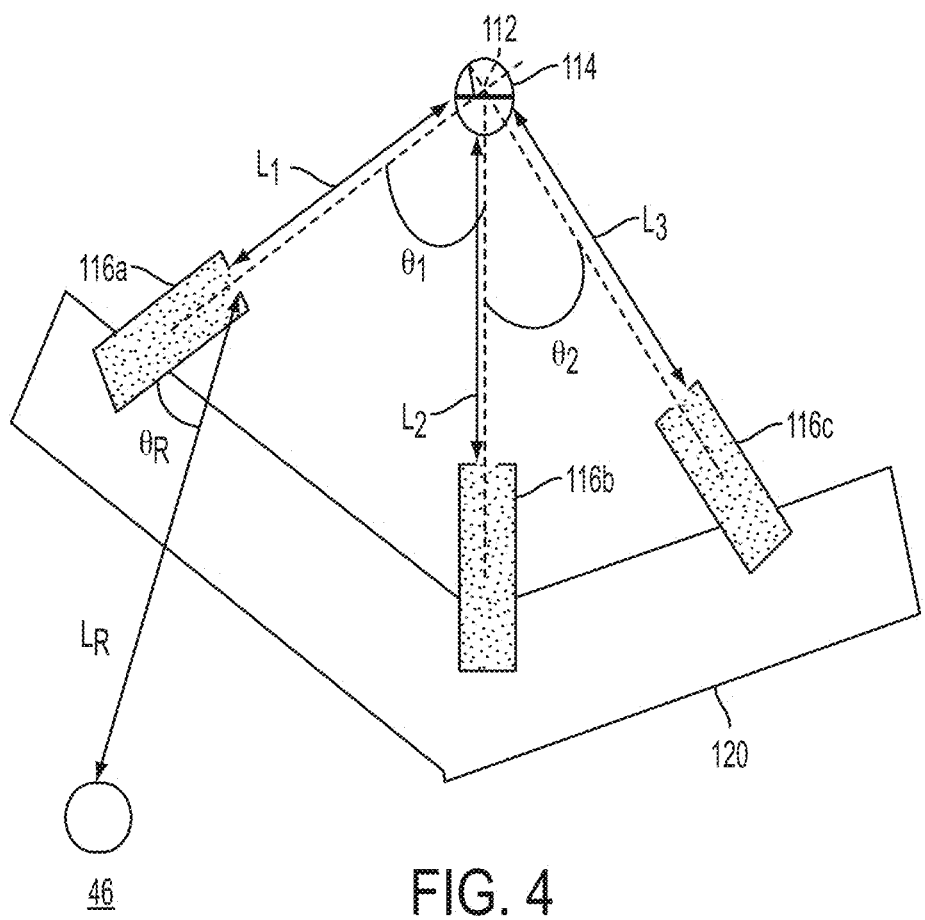
FIG. 4 is a diagram of probes positioned relative to an encapsulated dipole, according to an illustrative embodiment of the invention.

Turning now to FIG. 4, A Probe Positioning System (PPS) 120 positions at least three probes on the patient's body, with a known relation in space between the probes. The PPS preferably holds the Probes 116 in a stable manner at selected locations over the patient's body 102, and accurately reports the angles ($\theta_1$ and $\theta_2$) between the probes. This information together with the distances L1, L2, and L3 between the probes 116 and the dipole 112, as determined from the gate at which the Dipole rotation signal is maximal, is used for the triangulation determination of the relative position of the rotating dipole 112 in three dimensions. Additionally, the distance $L_R$ and angle $\theta_R$ between at least one of the Probes and at least one reference point 46 on or in the body, or on a probe (catheter) introduced into the body, as determined by a Doppler sensor, is preferably available. This information will enable the alignment of the PPS 120 with the patient body and target area as obtained by imaging obtained by other means. The angle data can be obtained either mechanical angle measuring systems or electronic solid-state positioning devices, both of which are conventional.

The system, which may be implemented using a microprocessor programmed to implement the algorithms described herein, receives all the collected data, i.e. the sensor positioning and the Doppler velocity and power values received from all sensors including the distance from the probe of each recording (gate). Using all this data, the system determines the position of the dipole capsule 114 in the framework of a coordinate system and with reference to the body anatomy as provided in an appropriate image. For example, first, on the basis of the distances and relative angles, the system can determine the position, (i.e. coordinates of the Dipole) in space using a conventional triangulation algorithm. Then, on the basis of the coordinates of the reference point, whether a recognizable anatomical point or another Dipole implanted or carried by a catheter, etc., as determined by one or more additional probes, the system can determine the location of the Dipole relative to the reference point, e.g. by matching the derived coordinates with those of the anatomical image.

Figure 5:
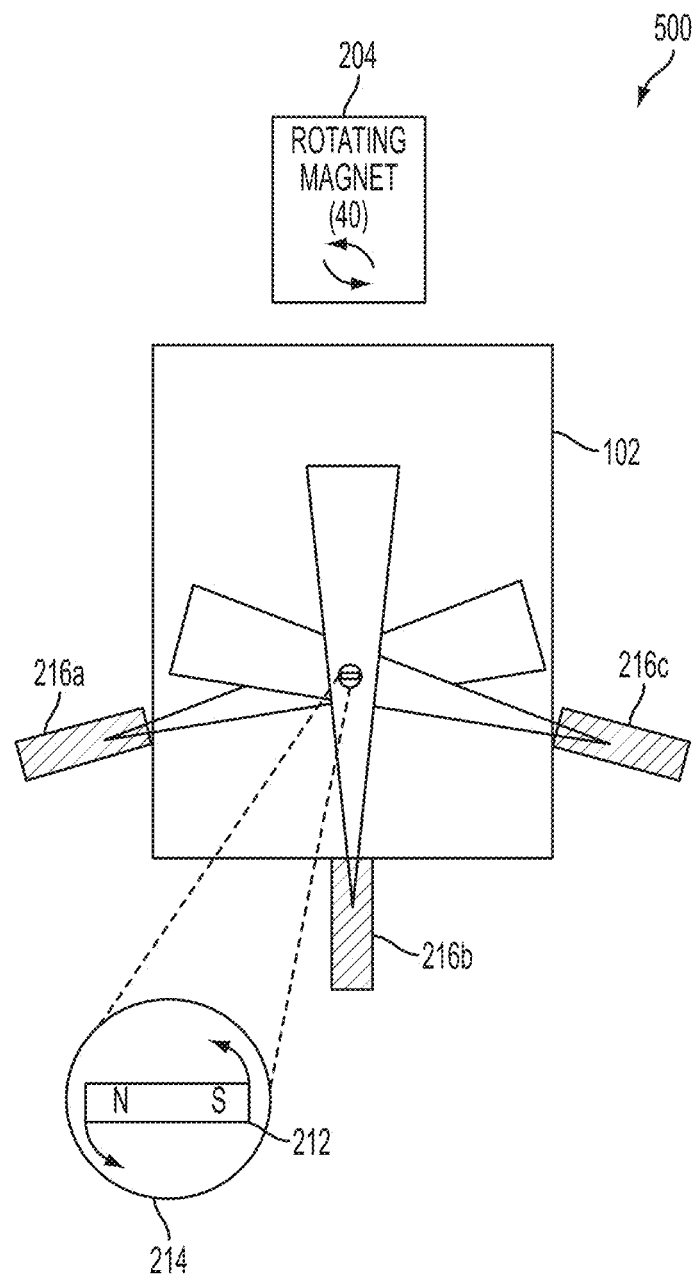
FIG. 5 is a block diagram of an exemplary system for detecting a position within a body, according to an illustrative embodiment of the invention that uses a magnetic dipole and a magnetic field.

FIG. 5 is a block diagram of an exemplary system 500 for detecting a position within a body 102, according to an illustrative embodiment of the invention that relies on a magnetic dipole and magnetic fields. The system includes a magnetic field generator 204, a magnetic dipole 212 within a capsule 214, and three Doppler transmitter/receiver probes, 216a, 216b, and 216c, generally Doppler transmitter/receiver probes 216. The rotating magnet can rotate at predetermined speeds (e.g., rates). When rotating, the rotating magnet induces a magnetic field in the area of the magnetic dipole 212. Magnetic dipoles can orient themselves along the lines of the magnetic field. So when the field changes direction, the magnetic dipole rotates in response to the rotating magnetic field.

In some embodiments, the magnetic field generator 204 is a permanent magnet (similar to those used in conventional magnetic stirrers). By using an appropriately strong permanent magnet, the magnetic field generator 204 can induce rotation of the magnetic dipole 212 when positioned within tens of centimeters of the dipole. Note that, unlike the electric fields discussed above, magnetic fields do not stimulate tissues and therefore low AC frequencies, 1-100 Hz can be readily used at any reasonable amplitude. At these frequencies a magnetic dipole in a capsule can rotate completely (i.e., make a full 360° rotation), and these frequencies are preferable because full rotations are easier to detect using Doppler ultrasound. At higher frequencies friction will limit the rotation and eventually there be reduced to smaller oscillations, which can be more difficult to detect using Doppler ultrasound.

In alternative embodiments, the rotating magnetic field may be achieved using three or more electromagnets, and phasing the power that is applied to the electromagnets in a conventional manner to make the magnetic field rotate.

In other alternative embodiments, instead of using a rotating magnetic field to make the magnetic dipole rotate, and alternating magnetic field may be used to make the dipole flip back and forth (in a manner similar to the flipping of the electric dipole discussed above). This embodiment may be implemented using a single electromagnet, and periodically reversing the direction of the applied current (e.g., using sinusoidal or square wave waveforms).

Once the magnetic field gets the magnetic dipole rotating or oscillating, the motion of the dipole is detected in the same manner discussed above in connection with the electric dipole embodiments. The PPS 120 depicted above in FIG. 4 is preferably also used in the magnetic embodiments in the same manner discussed above in connection with the electric dipole embodiments, and the subsequent processing to determine the location is also similar to the processing described above in connection with the electric dipole embodiments.

Figure 6:
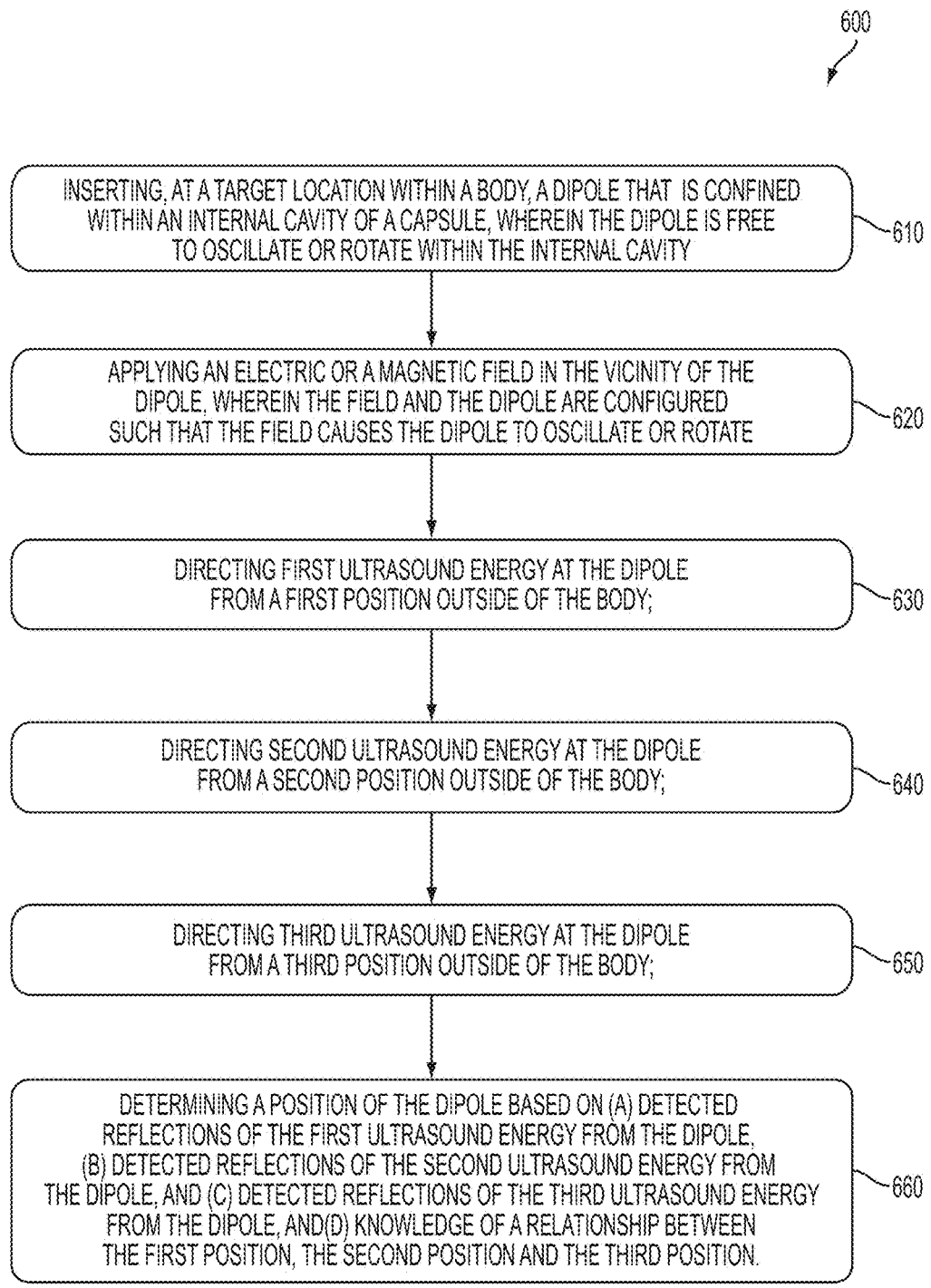
FIG. 6 is a flow diagram for a method of detecting a position within a body, according to an illustrative embodiment of the invention.

FIG. 6 is a flow diagram for a method 600 of detecting a position within a body. The method involves, inserting, at a target location within a body, a dipole (e.g., electric dipole 112 as shown above in FIG. 3 or magnetic dipole 212 as shown above in FIG. 5) that is confined within an internal cavity of a capsule (e.g., capsule 114 as shown above in FIG. 3) (Step 610) The dipole is free to oscillate or rotate within the internal cavity.

The method also involves, applying an electric or a magnetic field in the vicinity of the dipole, wherein the field and the dipole are configured such that the field causes the dipole to oscillate or rotate (Step 620). The applied electric field can be the electric field as described above with respect to FIG. 3. The applied magnetic field can be the magnetic field as described above with respect to FIG. 5.

The method also involves directing first ultrasound energy at the dipole from a first position outside of the body (Step 630). The method also involves directing second ultrasound energy at the dipole from a second position outside of the body. (Step 640). The method also involves directing third ultrasound energy at the dipole from a third position outside of the body (Step 650). The first, second and third ultrasound energy can be directed by Doppler transmitter/receiver probes (e.g., probes 116 as described above in FIG. 3). The Doppler transmitter/receiver probes can be part of a standard Doppler system that generates an ultrasound beam (8) and acts as a range detector by the use of multiple gates.

The method also involves determining a position of the dipole based on (a) detected reflections of the first ultrasound energy from the dipole, (b) detected reflections of the second ultrasound energy from the dipole, and (c) detected reflections of the third ultrasound energy from the dipole, and (d) knowledge of a relationship between the first position, the second position and the third position (Step 660). In some embodiments, the position of the dipole is described in a three dimensional coordinate plane. The three dimensional coordinates of the dipole can be obtained by measuring a distance from Doppler transmitter/receiver probes using triangulation.

In alternative embodiments, the dipole, without being in a capsule, is inserted into the body. In these embodiments, the applied field may still be able to cause the dipole to oscillate (i.e., vibrate) within the body. For example, a dipole can be inserted into biological tissue, and then oscillate within the tissue in response to an applied field. The oscillations are then detected using Doppler ultrasound in a manner similar to the way the rotation is detected in the embodiments described above.

In alternative embodiments, only one or two Doppler transmitter/receiver probes are used. In these embodiments, the Doppler measurement can be considered along with additional information obtained from a CAT scan and/or MRI of the target area to determine the position of the dipole.

Figure 7:
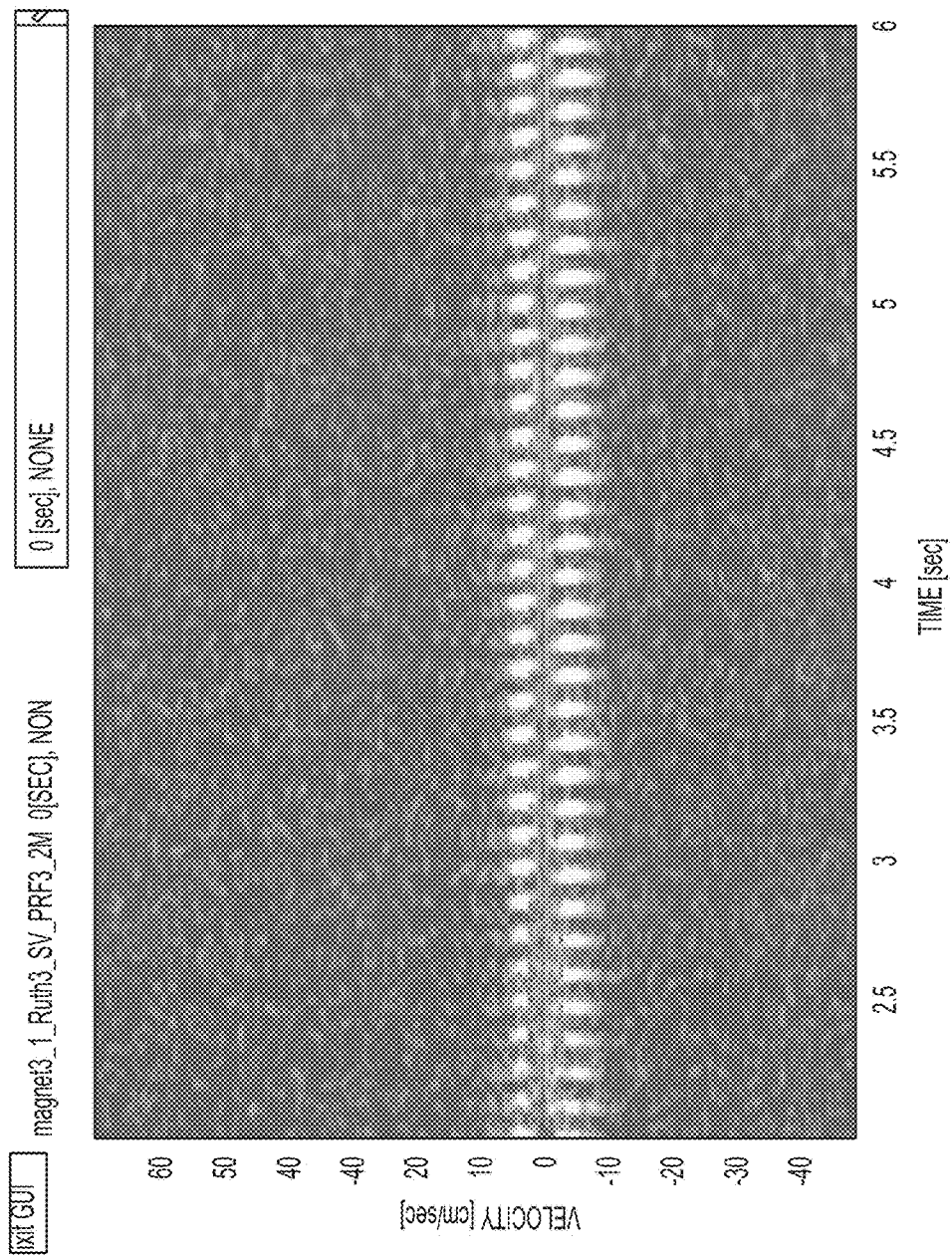
FIG. 7 is a graph showing exemplary Doppler velocity signal versus time, according to an illustrative embodiment of the invention.

FIG. 7 is a graph showing Doppler velocity vs. time signals obtained during an experiment in which a 2 mm magnetic dipole was placed in a capsule that is filled with a physiological solution, and the capsule was positioned in a large water tank. Rotation of the dipole was induced by a rotation inductor positioned outside of the large water tank at a distance of about 15 cm from the dipole. The ultrasound probe was located at a distance of about 10 cm from the dipole. As shown in FIG. 7, the Doppler rotation velocity signal has periodic peaks of velocity and power. The periodic peaks of velocity and power are synchronized with the dipole rotation. The Doppler rotation velocity signal disappears when rotation of the dipole stops and periodicity of the Doppler rotation velocity signal changes in sync with the changes in rotation speed of the dipole. Note that in alternative embodiments, the power could be displayed on the Y-axis instead of the velocity.

Figure 8:
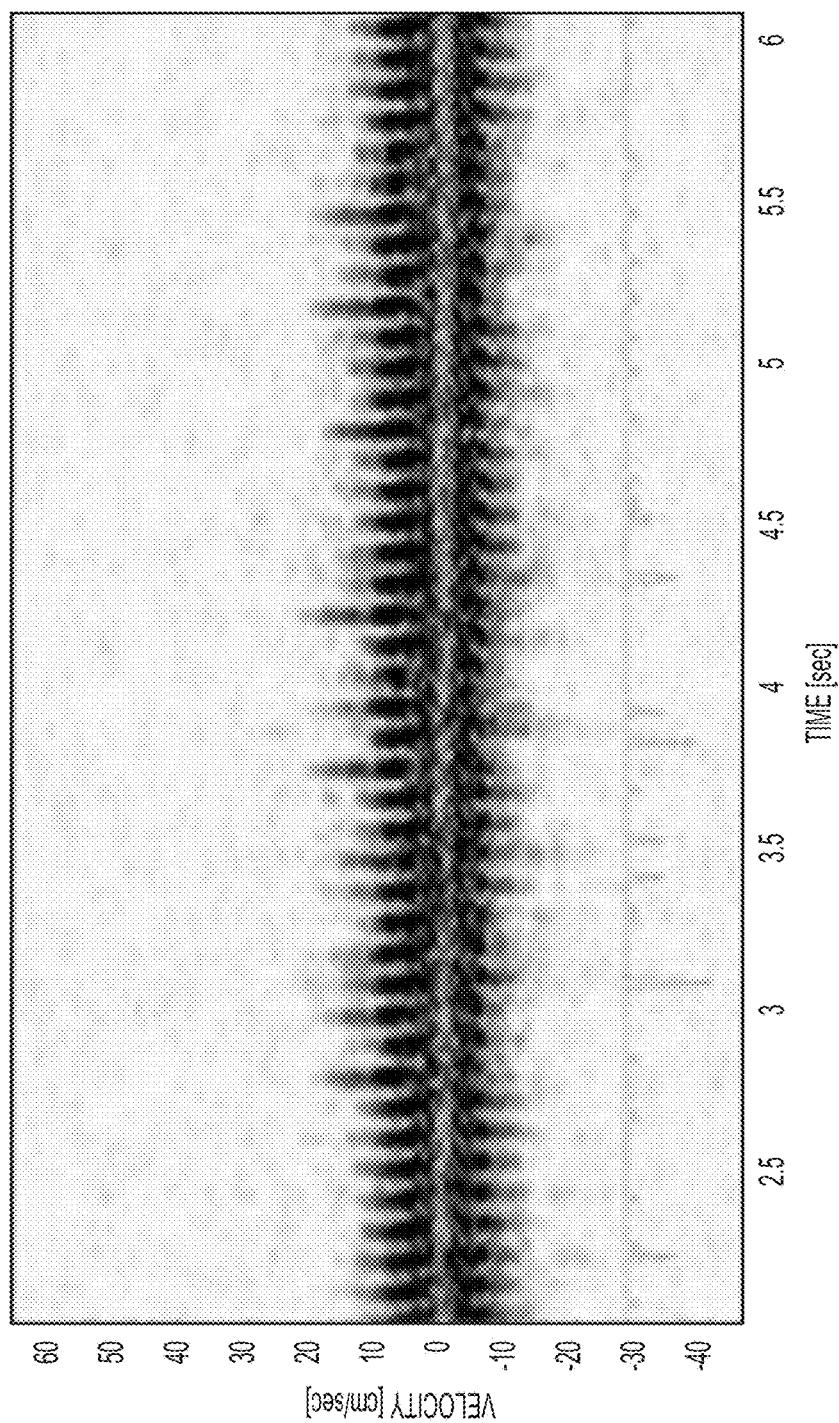
FIG. 8 is a graph showing exemplary Doppler rotation velocity signal versus time, according to an illustrative embodiment of the invention.
Figure 9A:
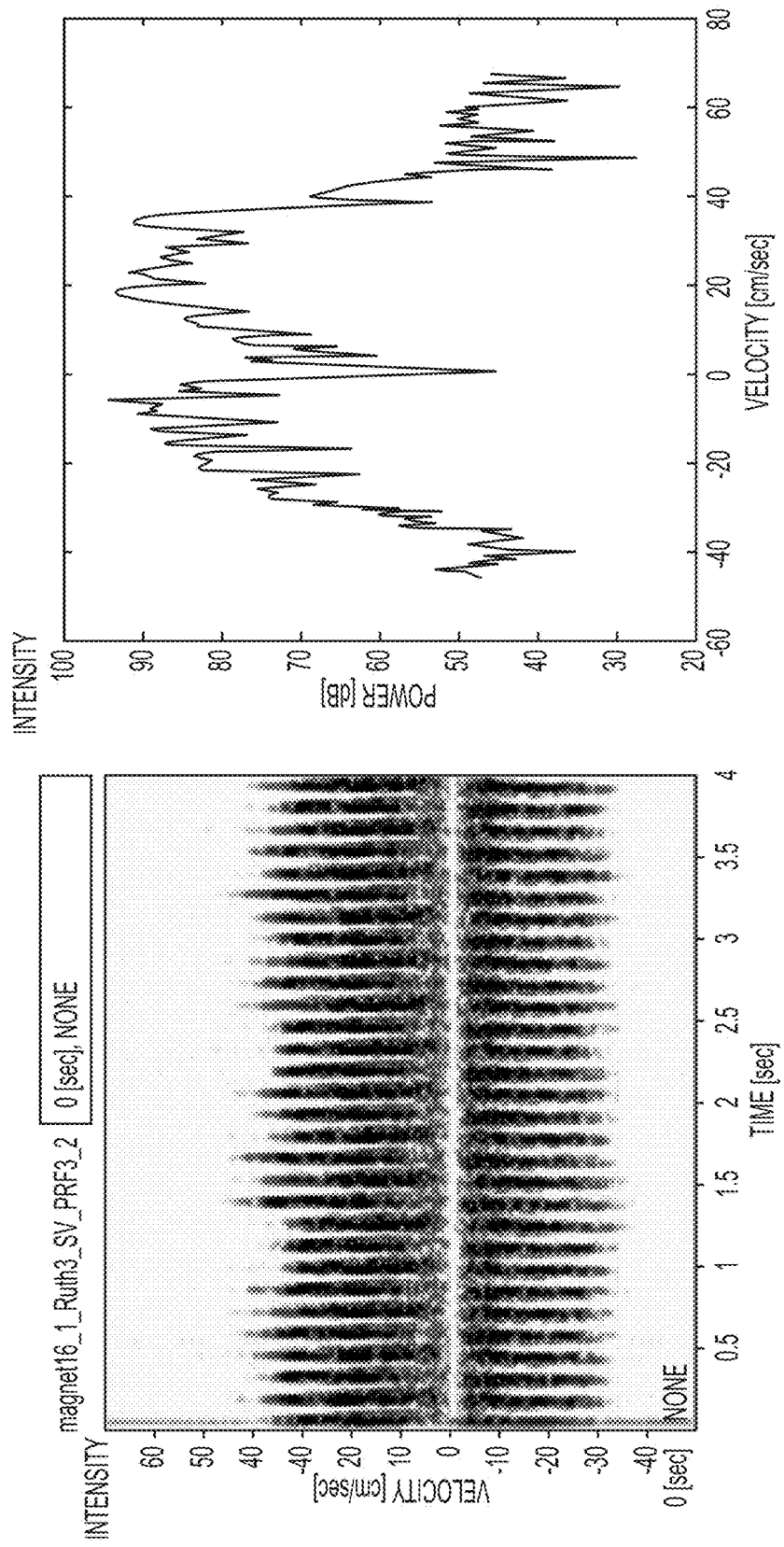
FIGS. 9A-9F are graphs showing exemplary Doppler rotation velocity signals versus time, according to illustrative embodiments of the invention.
Figure 9B:
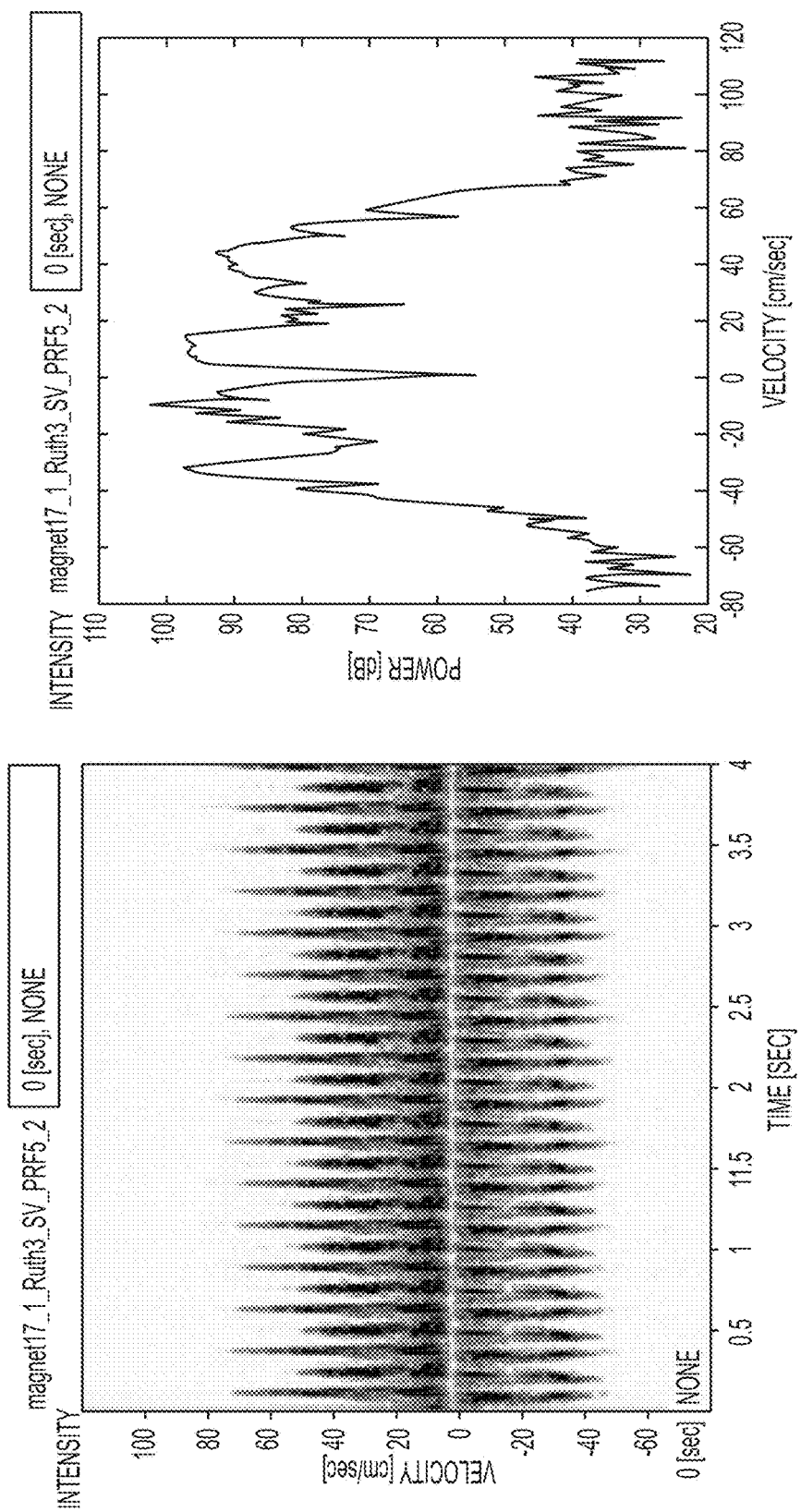
Figure 9C:
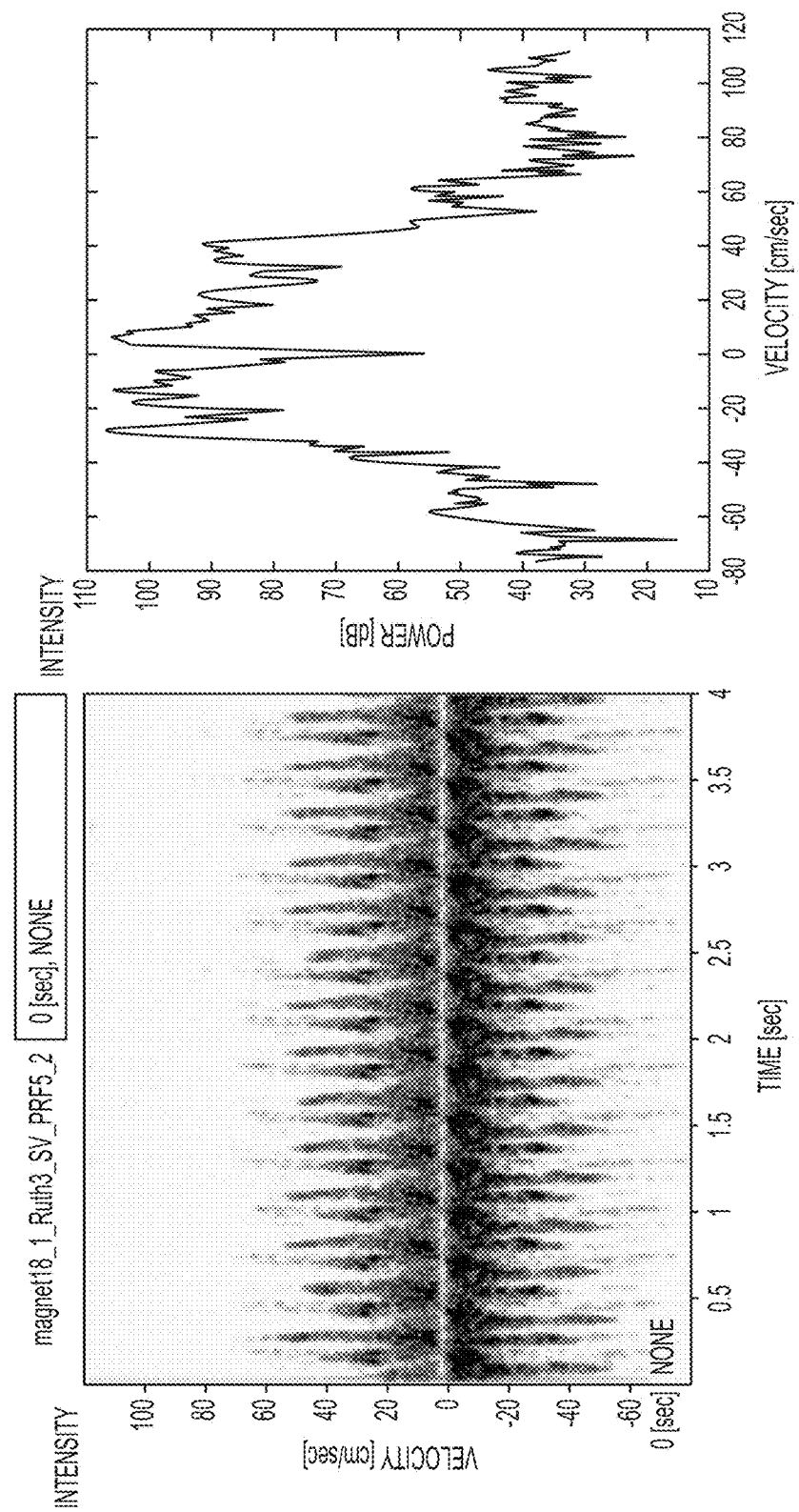
Figure 9D:
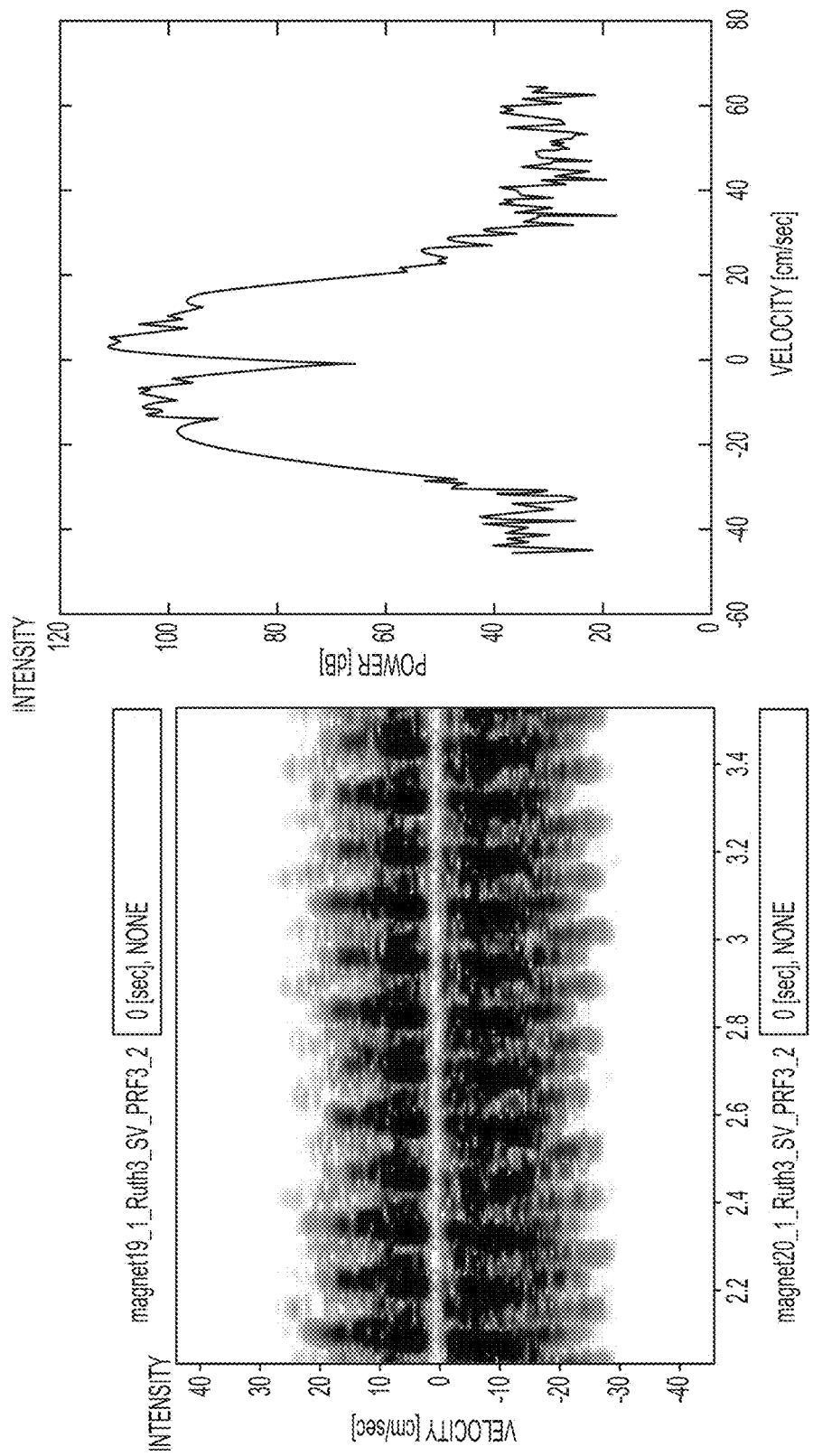
Figure 9E:
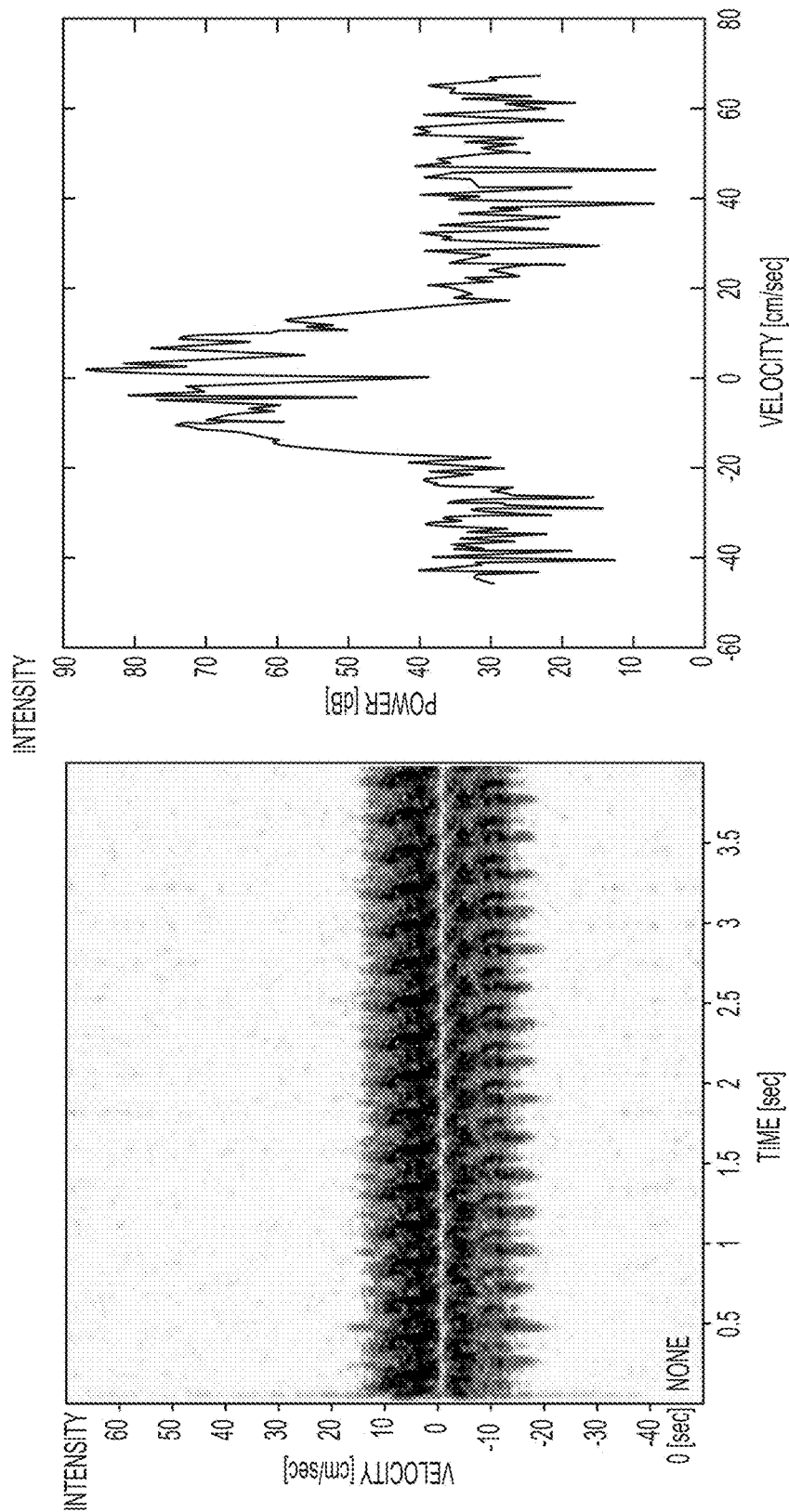
Figure 9F:
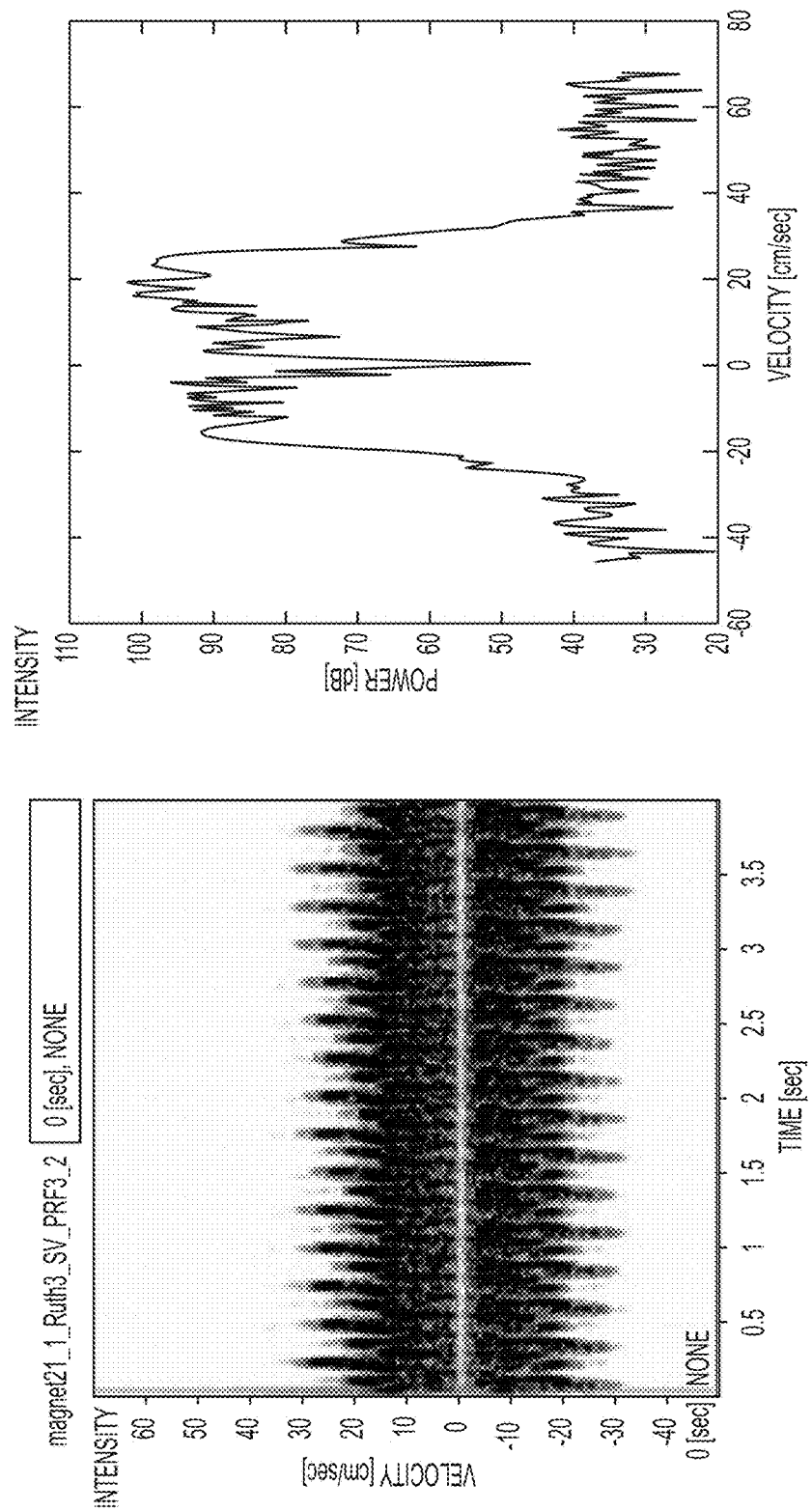

FIG. 8 is a graph showing exemplary Doppler velocity signal vs. time that was obtained in a second experiment. The dipole and capsule were positioned on one side of a human thigh, and a rotating inductor and ultrasound probe were positioned on the other side of the human thigh, at a distance of about 15 cm from the dipole. FIG. 8 shows the Doppler velocity signals that were thus obtained through the human thigh. This experiment verifies that clear and strong signals that can well serve to identify and determine the location of the Dipole can be obtained through living tissue.

In some embodiments, more than one rotating dipole is inserted into the body. In these embodiments, recognition between each dipole can be achieved by discerning the different patterns of movement of each dipole.

FIGS. 9A-9F are multiple graphs showing exemplary Doppler velocity signals vs. time, obtained as measured from the rotation of dipoles of different shapes. FIG. 9A-9F correspond to the different types of magnetic Dipoles A-F depicted in FIG. 2. The various shaped dipoles can be identified by certain characteristics of their corresponding Doppler rotation velocity signals. For example, the rotation of the symmetric dipoles A & D from FIG. 2 produces pulses of similar amplitude and with symmetric power spectra. The larger terminal bodies in Dipole D produce much stronger signals (110 dB for dipole D vs. 90 dB for dipole A). The non-symmetric dipoles B & F from FIG. 2 produce alternating large & small Doppler velocity signals that correspond to the differences in their moving terminal bodies and yield a corresponding non-symmetric power spectra. Thus, if a number of capsules containing different shaped dipoles are implanted in the same area of a body, the system would be able to distinguish between the various dipoles based on the nature of their Doppler signals.

While the invention has been particularly shown and described with reference to specific embodiments, it should be understood by those skilled in the art that various changes in form and detail may be made therein without departing from the spirit and scope of the invention as defined by the appended claims.

The invention claimed is:

1. A method of detecting a position within a body, the method comprising:
   inserting, at a target location within a body, a dipole that is confined within an internal cavity of a capsule, wherein the dipole is free to oscillate or rotate within the internal cavity;
   applying an electric or a magnetic field in the vicinity of the dipole, wherein the field and the dipole are configured such that the field causes the dipole to oscillate or rotate;

directing first ultrasound energy at the dipole from a first position outside of the body;
detecting reflections of the first ultrasound energy from the dipole;
directing second ultrasound energy at the dipole from a second position outside of the body;
detecting reflections of the second ultrasound energy from the dipole;
directing third ultrasound energy at the dipole from a third position outside of the body;
detecting reflections of the third ultrasound energy from the dipole; and
determining a position of the dipole based on
(a) the detected reflections of the first ultrasound energy from the dipole,
(b) the detected reflections of the second ultrasound energy from the dipole,
(c) the detected reflections of the third ultrasound energy from the dipole, and
(d) knowledge of a relationship between the first position, the second position and the third position.

2. The method of claim 1, wherein the determining step uses pulsed ultrasound Doppler to detect time-varying velocities of the dipole, and the position of the dipole is determined based on the detected time-varying velocities.

3. The method of claim 1, wherein the steps of directing the first ultrasound energy, directing the second ultrasound energy, and directing the third ultrasound energy are performed simultaneously.

4. The method of claim 1, wherein the body is a human being.

5. The method of claim 1, wherein the body is an animal.

6. The method of claim 1 wherein the body is a member configured to be placed within a living being.

7. The method of claim 1 wherein the field is an electric field and the dipole is an electric dipole.

8. The method of claim 1 wherein the field is a magnetic field and the dipole is a magnetic dipole.

9. The method of claim 1 wherein the field has a magnitude and frequency that does not stimulate biological tissue.

10. The method of claim 1 wherein the frequency of the field is greater than 100 kHz.

11. An apparatus for insertion into biological tissue, the apparatus comprising:
a capsule that defines a sealed internal cavity, the capsule having a biocompatible outer surface, the internal cavity being substantially spherical; and
a dipole positioned in the internal cavity, the capsule and the dipole each shaped such that the dipole is capable of oscillating or rotating within the internal cavity in response to an applied field, the dipole including a rod with a length between 0.5 and 1 mm long, wherein
the dipole rotates within the internal cavity around a rotation axis in response to the applied field,
the rod is centered on the rotation axis, and
the rod is elongated in a direction perpendicular to the rotation axis.

12. The apparatus of claim 11 wherein the dipole consists of a biocompatible material.

13. The apparatus of claim 11 wherein the outer surface of the capsule comprises silicone.

14. The apparatus of claim 11 wherein the outer surface of the capsule comprises carbon.

15. The apparatus of claim 11 wherein the outer surface of the capsule comprises polytetrafluoroethylene.

16. The apparatus of claim 11, wherein the dipole is a cross that includes said rod.

17. The apparatus of claim 11, wherein the dipole includes spheres attached at each end of the rod.

18. The apparatus of claim 11 wherein the dipole is an electric dipole that oscillates or rotates in response to an alternating or rotating electric field.

19. The apparatus of claim 11 wherein the dipole is a magnetic dipole that oscillates or rotates in response to an alternating or rotating magnetic field.

20. The apparatus of claim 11 wherein the internal cavity is filled with air.

21. The apparatus of claim 11 wherein the internal cavity is filled with gas.

22. The apparatus of claim 11 wherein the internal cavity holds at least a partial vacuum.

23. The apparatus of claim 11 wherein the dipole comprises a dielectric material that can retain an electric charge for at least one month.

24. The apparatus of claim 11, wherein the dipole comprises a synthetic polymer material.

25. The apparatus of claim 11, wherein the dipole comprises a Ferroelectric material.

26. A method of detecting a position within a body, the method comprising:
inserting, at a target location within a body, a dipole that is able to oscillate within the body;
applying an electric or a magnetic field in the vicinity of the dipole, wherein the field and the dipole are configured such that the field causes the dipole to oscillate;
directing first ultrasound energy at the dipole from a first position outside of the body;
detecting reflections of the first ultrasound energy from the dipole;
directing second ultrasound energy at the dipole from a second position outside of the body;
detecting reflections of the second ultrasound energy from the dipole;
directing third ultrasound energy at the dipole from a third position outside of the body;
detecting reflections of the third ultrasound energy from the dipole; and
determining a position of the dipole based on
(a) the detected reflections of the first ultrasound energy from the dipole,
(b) the detected reflections of the second ultrasound energy from the dipole,
(c) the detected reflections of the third ultrasound energy from the dipole, and
(d) knowledge of a relationship between the first position, the second position and the third position.

27. A method of detecting a position within a body, the method comprising:
inserting, at a target location within a body, a dipole that is able to oscillate or rotate within the body;
applying an electric or a magnetic field in the vicinity of the dipole, wherein the field and the dipole are configured such that the field causes the dipole to oscillate or rotate;
directing first ultrasound energy at the dipole from a first position outside of the body;
detecting reflections of the first ultrasound energy from the dipole;
receiving imaging information for the target location within the body; and
determining a position of the dipole based on
(a) the detected reflections of the first ultrasound energy from the dipole, and
(b) the imaging information for the target location.

28. The method of claim 27 wherein the imaging information is obtained from a CAT scan.

29. The method of claim 27 wherein the imaging information is obtained from a MRI image.

30. The method of claim 27, further comprising:
directing second ultrasound energy at the dipole from a second position outside of the body; and
detecting reflections of the second ultrasound energy from the dipole, wherein the step of determining the position of the dipole is further based on the detected reflections of the second ultrasound energy from the dipole.

* * * * *